United States Patent
Scharlack et al.

(10) Patent No.: US 9,504,541 B2
(45) Date of Patent: Nov. 29, 2016

(54) METHOD AND SYSTEM FOR DESIGNING CUSTOM RESTORATIONS FOR DENTAL IMPLANTS

(75) Inventors: Ronald S. Scharlack, Brookline, MA (US); Alexander Yarmarkovich, Swampscott, MA (US); Bethany Grant, Scituate, MA (US)

(73) Assignee: DENTSPLY International Inc., York, PA (US)

( * ) Notice: Subject to any disclaimer, the term of this patent is extended or adjusted under 35 U.S.C. 154(b) by 1686 days.

(21) Appl. No.: 11/325,990

(22) Filed: Jan. 5, 2006

(65) Prior Publication Data

US 2007/0154868 A1    Jul. 5, 2007

(51) Int. Cl.
*A61C 5/00* (2006.01)
*A61C 13/00* (2006.01)
*A61C 5/10* (2006.01)
*A61C 13/09* (2006.01)

(52) U.S. Cl.
CPC ............ *A61C 13/0004* (2013.01); *A61C 5/10* (2013.01); *A61C 13/09* (2013.01)

(58) Field of Classification Search
CPC ........................................... A61C 5/00
USPC ........................... 700/97; 433/215, 172, 223
See application file for complete search history.

(56) References Cited

U.S. PATENT DOCUMENTS

| | | |
|---|---|---|
| 5,674,069 A | 10/1997 | Osorio |
| 5,989,029 A | 11/1999 | Osorio et al. |
| 6,231,342 B1 | 5/2001 | Osorio et al. |
| 6,398,554 B1 | 6/2002 | Perot et al. |
| 6,788,986 B1 | 9/2004 | Traber et al. |
| 2004/0167646 A1 | 8/2004 | Jelonek et al. |
| 2004/0185422 A1 | 9/2004 | Orth et al. |
| 2005/0089822 A1* | 4/2005 | Geng ............................ 433/215 |

FOREIGN PATENT DOCUMENTS

| | | |
|---|---|---|
| DE | 10300301 A1 | 7/2004 |
| EP | 1561433 A | 8/2005 |
| JP | 2001-54525 A | 2/2001 |
| JP | 2001-507264 A | 6/2001 |

OTHER PUBLICATIONS

English language translation of Notice of Reasons for Rejection dated Feb. 28, 2012, in Japanese Patent Application No. 2008-549507.
Office Action dated Oct. 25, 2010, in Chinese Application No. 200680053714.2.

* cited by examiner

*Primary Examiner* — Tejal Gami
(74) *Attorney, Agent, or Firm* — David A. Zdurne; Douglas J. Hura; Leana Levin

(57) ABSTRACT

A method of designing a dental restoration component. A set of design dimensional constraints is defined which must be satisfied for the dental restoration component. A set of design parameters for the dental restoration component also is defined. Using at least in part a penalty function, a value is assigned to each of said design parameters for the dental restoration component, consistent with the constraints for said component, said penalty function taking into account at least more than one of said design parameters and which signals a constraint being reached when the value of any of said parameters violates a constraint.

13 Claims, 9 Drawing Sheets

METHOD AND SYSTEM FOR DESIGNING CUSTOM RESTORATIONS FOR DENTAL IMPLANTS

BACKGROUND OF INVENTION

1. Field of Invention

This invention relates to the field of dental restorations, particularly implant dentistry. In particular, it relates to interrelating the design of custom abutments and the planning of restorations such as crowns and bridges, to the design of combined abutment-crowns, and to the planning of implant placement.

2. Background

Dental restorations systems seek to provide cosmetic and functional replacements for missing teeth. A dental restorative system that replaces a single tooth typically includes three components: the dental implant fixture, the abutment, and a crown. When more than on tooth is being replaced, a bridge may be used instead of a crown for each replaced tooth.

The dental implant fixture anchors the restorative system to the jawbone. The crown replicates the contour and appearance of the visible portion of the restorative system, to match that of the natural dentition. Finally, the abutment connects the crown to the dental implant fixture. The abutment also holds the crown in proper position and alignment relative to the implant fixture, and absorbs the stress of chewing. Standard methods for preparing dental restorative systems require considerable time, labor and expense. U.S. Pat. No. 6,231,342 explains a standard method involving between six and ten trips of patient to a dentist's office to complete installation of a restorative system. Using more advanced techniques and equipment such as those discussed in U.S. Pat. Nos. 5,674,069, 5,989,029 and 6,231,342, for example, the number of visits to the dentist's office may be reduced, as well as the cost of the restoration. At the same time, the quality of the restoration may be improved. The three-above identified patents teach the design of a custom abutment. In part, measurements are utilized of the position and orientation both of the implant fixture and of the edentulous space. These measurements, along with information about the type of tooth being replaced, allow an abutment and tooth profile to be defined. The abutment approximates the profile of the tooth in reduced size, except in the transition emergence profile region, to match the tooth (i.e., crown) shape with that of the implant.

The abutment must be designed not only to match the tooth profile, but also to meet other constraints such as angular orientation relative to other abutments in the restoration, angular orientation relative to the implant, angle of the emergence profile of the abutment from the implant, the combined thickness of the abutment and crown material, covering of the retaining screw, and so forth. These constraints limit the acceptable abutment and crown designs. These limitations are even more acute in cases where multiple implants are involved and multiple implant replacements limit the range of acceptable restorations.

Consequently, though there has been technology to produce customized abutments, nonetheless substantial manual work has been required to match the requirements of crowns and bridges with those of abutments. Considerable cost savings would be achievable, and the number of patient visits to the dental restoration team reduced, if the design and manufacture of the crown or bridge could be automated (in full or in part), in conjunction with the automation for abutments. Of course, there may be competing and interacting design constraints when both an abutment and a crown are to be designed (and manufactured) concurrently.

A need exists, therefore, for a method and apparatus that will permit automated design and manufacture of abutments, crowns (etc.) and abutment-crown combinations, or other dental restoration components or combinations of components.

SUMMARY OF INVENTION

In accordance with aspects of the invention, some embodiments aid in the design of tooth replacement, including abutments, crowns and combined abutment-crowns, by incorporating the above-mentioned constraints into the measurement and design process. Thus, the shape, size and orientation of the desired restoration may be controlled by the constraints so that the designer is assisted in planning the restoration. Since both the abutment and crown (or bridge) constraints are incorporated into the measurement and design process, the resulting design should be manufacturable without further significant technician involvement.

Such systems and methods support the creation of a plan for dental implant placement that includes the design of the abutment and crown. Limitations such as the location of bone with sufficient density to support the implant and the location of nerves and other anatomical features introduce additional constraints on the prosthesis design. All of these constraints are taken into account in the design process to realize a restoration consistent with the complete set of constraints.

The invention comprises a number of aspects. According to a first aspect, a computer-implemented method is provided for specifying design parameters for at least first and second dental restoration components (e.g., implants, abutments, copings and crowns) that must be installed in a cooperating relationship. Such a method comprises: receiving a set of design dimensional constraints which must be satisfied for each of the first and second dental restoration components; receiving a set of design parameters for each of the first and second dental restoration components; and assigning values to the design parameters of the first and second dental components such that there are not conflicts between the design parameter values and the design constraints.

According to a second aspect, a computer-implemented method is provided for specifying design parameters for at least first and second dental restoration components that must be installed in a cooperating relationship. Such a method comprises: receiving a set of design dimensional constraints which must be satisfied for each of the first and second dental restoration components; receiving a set of design parameters for each of the first and second dental restoration components; for the first dental restoration component, assigning a value to each of said design parameters, consistent with the constraints for said component; for the second dental restoration component, determining whether there is a conflict between possible values for a design parameter and the dimensional constraints for the first component and, if there is a conflict, changing a value of at least one design parameter for the first component and re-determining whether there is a conflict, until no conflict exists or it is established that for all values of the design parameters for the first component there will be conflict; assigning a value to a first design parameter of the second dental restoration component, consistent with all constraints; and repeating the preceding two acts until values have been assigned to all design parameters of the first and second components and no constraint or parameter value conflicts exist. Such a method may further include recording said assigned parameter values in a data structure on a computer-readable medium. In addition to recording, the method may further include operating a computer-aided manufacturing system in accordance with said values in said data structure, to manufacture said first and second components.

According to a third aspect, there is shown a computer-implemented method of designing a dental restoration component, comprising: receiving a set of design dimensional constraints which must be satisfied for the dental restoration component; receiving a set of design parameters for the dental restoration component; receiving a definition for a penalty function which takes into account at least more than one of said design parameters and which signals a constraint being reached when the value of any of said parameters violates a constraint; and using the penalty function, assigning a value to each of said design parameters for the dental restoration component, consistent with the constraints for said component. The penalty function may be used to assist, along with other factors, assigning a value to at least one of said design parameters. The signaling of a constraint being reached may involve the penalty function transitioning to a predetermined value.

According to a fourth aspect, a computer-implemented method of designing a dental restoration component is shown, comprising: receiving a set of design dimensional constraints which must be satisfied for the dental restoration component; receiving a set of design parameters for the dental restoration component; and using at least in part a penalty function, assigning a value to each of said design parameters for the dental restoration component, consistent with the constraints for said component, said penalty function taking into account at least more than one of said design parameters and which signals a constraint being reached when the value of any of said parameters violates a constraint. Assigning a value to each of said design parameters may comprise assigning said values consistent with the corresponding value of the penalty function being at or near an extreme value of the penalty function. The extreme value may be a minimum value. Assigning the value to each of said design parameters is not limited to using the penalty function to do so. The method may also include recording said assigned parameter values in a data structure on a computer-readable medium. In addition, the method may include operating a computer-aided manufacturing system in accordance with said values in said data structure, to manufacture at least one of said first and second components.

According to a fifth aspect, there is shown a computer-implemented method of designing an optimized dental restoration component, comprising: receiving a set of design dimensional constraints which must be satisfied for the component; receiving a set of design parameters for the component; assigning a value to each of said design parameters, consistent with the constraints for said component; determining whether there is a conflict between possible values for a design parameter and the dimensional constraints for the component and, if there is a conflict, changing a value of at least one design parameter for the component and re-determining whether there is a conflict, until no conflict exists or it is established that for all values of the design parameters for the component there will be conflict; repeating the "assigning" operation until values have been assigned to all design parameters of the component and no constraint or parameter value conflicts exist; and executing a penalty function to calculate an acceptable set of design parameter values for the component. Such a method may further include recording said acceptable set of parameter values in a data structure on a computer-readable medium. It also may include operating a computer-aided manufacturing system in accordance with said acceptable set of values in said data structure, to manufacture said component.

According to a sixth aspect, there is shown a computer-implemented method for specifying a least one common design feature for at least first and second dental restoration components that must be installed in a cooperating relationship, said method comprising: receiving a set of design dimensional constraints which must be satisfied for each of the first and second dental restoration components; receiving a set of design parameters for each of the first and second dental restoration components; and assigning values to the common design feature for said first and second dental components such that there is an absence of conflicts between the design parameters and the design constraints of said components. The first and second components may comprise an abutment and a crown, and the at least one common design feature may be a common margin for the abutment and crown.

According to a seventh aspect, a method is taught for designing at least first and second dental restoration components that must be installed in a cooperating relationship, said method comprising: defining a set of design dimensional constraints which must be satisfied for each of the first and second dental restoration components; defining a set of design parameters for each of the first and second dental restoration components; and assigning values to the first and second dental components such that there is an absence of conflicts between the design parameters and the design constraints.

According to an eighth aspect, a method is shown for specifying design parameters for at least first and second dental restoration components that must be installed in a cooperating relationship, comprising, with a computer system: defining a set of design dimensional constraints which must be satisfied for each of the first and second dental restoration components; defining a set of design parameters for each of the first and second dental restoration components; for the first dental restoration component, assigning a value to each of said design parameters, consistent with the constraints for said component; for the second dental restoration component, determining whether there is a conflict between possible values for a design parameter and the dimensional constraints for the first component and, if there is a conflict, changing a value of at least one design parameter for the first component and re-determining whether there is a conflict, until no conflict exists or it is established that for all values of the design parameters for the first component there will be conflict; assigning a value to a first design parameter of the second dental restoration component, consistent with all constraints; and repeating the previous two operations until values have been assigned to all design parameters of the first and second components and no constraint or parameter value conflicts exist. In addition, said assigned parameter values may be recorded in a data structure on a computer-readable medium. Further, a computer-aided manufacturing system may be operated in accordance with said values in said data structure, to manufacture at least one of said first and second components.

According to a ninth aspect, a method is taught of designing a dental restoration component, comprising: defining a set of design dimensional constraints which must be satisfied for the dental restoration component; defining a set of design parameters for the dental restoration component; defining for a penalty function which takes into account at least more than one of said design parameters and which signals a constraint being reached when the value of any of said parameters violates a constraint; and using the penalty function, assigning a value to each of said design parameters for the dental restoration component, consistent with the constraints for said component. The penalty function may be used to assist, along with other factors, assigning a value to at least one of said design parameters.

According to a tenth aspect, a method is provided for of designing a dental restoration component, comprising: defining a set of design dimensional constraints which must be satisfied for the dental restoration component; defining a set of design parameters for the dental restoration component; and using at least in part a penalty function, assigning a value to each of said design parameters for the dental restoration component, consistent with the constraints for said component, said penalty function taking into account at least more than one of said design parameters and which signals a constraint being reached when the value of any of said parameters violates a constraint. Assigning a value to each of said design parameters comprises assigning said values consistent with the corresponding value of the penalty function being at or near an extreme value of the penalty function. The extreme value may be, and usually is, a minimum value. Assigning the value to each of said design parameters is not limited to using the penalty function to do so. The assigned parameter values may be recorded in a data structure on a computer-readable medium. The method may also include operating a computer-aided manufacturing system in accordance with the assigned values, including (but not limited to) values in said data structure, to manufacture said first and second components.

According to an eleventh aspect, there is shown a method of designing an optimized dental restoration component, comprising: defining a set of design dimensional constraints which must be satisfied for the component; defining a set of design parameters for the component; assigning a value to each of said design parameters, consistent with the constraints for said component; determining whether there is a conflict between possible values for a design parameter and the dimensional constraints for the component and, if there is a conflict, changing a value of at least one design parameter for the component and re-determining whether there is a conflict, until no conflict exists or it is established that for all values of the design parameters for the component there will be conflict; repeating the determining operation until values have been assigned to all design parameters of the component and no constraint or parameter value conflicts exist; and using a penalty function to calculate an acceptable set of design parameter values for the component. Such a method may further include recording said calculated set of parameter values in a data structure on a computer-readable medium. It also may further include operating a computer-aided manufacturing system in accordance with said calculated set of values in said data structure, to manufacture said component.

According to a twelfth aspect, a method is provided for specifying a least one common design feature for at least first and second dental restoration components that must be installed in a cooperating relationship, said method comprising: providing a set of design dimensional constraints which must be satisfied for each of the first and second dental restoration components; providing a set of design parameters the at least one common design feature for each of the first and second dental restoration components; and assigning values to the common design feature for said first and second dental components such that there is an absence of conflicts between the values of said design parameters and the design constraints of said components. The first and second components comprise an abutment and a crown, and the at least one common design feature may a common margin for the abutment and crown.

According to a thirteenth aspect, there is disclosed an article comprising a computer-readable signal, recorded on a computer-readable medium, and comprising instructions which, when executed, cause a computer system to perform a method for specifying design parameters for at least first and second dental restoration components that must be installed in a cooperating relationship, said method comprising: receiving a set of design dimensional constraints which must be satisfied for each of the first and second dental restoration components; receiving a set of design parameters for each of the first and second dental restoration components; and assigning values to the first and second dental components such that there is an absence of conflicts between the design parameters and the design constraints.

According to a fourteenth aspect, there is disclosed an article comprising a computer-readable signal, recorded on a computer-readable medium, and comprising instructions which, when executed, cause a computer system to perform a method of specifying design parameters for at least first and second dental restoration components that must be installed in a cooperating relationship, comprising: receiving a set of design dimensional constraints which must be satisfied for each of the first and second dental restoration components; receiving a set of design parameters for each of the first and second dental restoration components; for the first dental restoration component, assigning a value to each of said design parameters, consistent with the constraints for said component; for the second dental restoration component, determining whether there is a conflict between possible values for a design parameter and the dimensional constraints for the first component and, if there is a conflict, changing a value of at least one design parameter for the first component and re-determining whether there is a conflict, until no conflict exists or it is established that for all values of the design parameters for the first component there will be conflict; assigning a value to a first design parameter of the second dental restoration component, consistent with all constraints; and repeating the two preceding acts until values have been assigned to all design parameters of the first and second components and no constraint or parameter value conflicts exist. The method may further include operating a computer-aided manufacturing system in accordance with said assigned values, to manufacture at least one of said first and second components.

According to a fifteenth aspect, there is discussed an article comprising a computer-readable signal, recorded on a computer-readable medium, and comprising instructions which, when executed, cause a computer system to perform a method of designing a dental restoration component, comprising: receiving a set of design dimensional constraints which must be satisfied for the dental restoration component; receiving a set of design parameters for the dental restoration component; receiving a definition for a penalty function which takes into account at least more than one of said design parameters and which signals a constraint being reached when the value of any of said parameters violates a constraint; and using the penalty function, assigning a value to each of said design parameters for the dental restoration component, consistent with the constraints for said component. The instructions when executed may further cause the penalty function to be used to assist, along with other factors, assigning a value to at least one of said design parameters.

According to a sixteenth aspect, an article is disclosed, comprising a computer-readable signal, recorded on a computer-readable medium, and comprising instructions which, when executed, cause a computer system to perform a method of designing a dental restoration component, comprising: receiving a set of design dimensional constraints which must be satisfied for the dental restoration component; receiving a set of design parameters of said parameters for the dental restoration component; and using at least in part a penalty function, assigning a value to each of said design parameters for the dental restoration component, consistent with the constraints for said component, said penalty function taking into account at least more than one of said design parameters and which signals a constraint being reached when the value of any of said parameters violates a constraint. Assigning a value to each of said design parameters may comprise assigning said values consistent with the corresponding value of the penalty function being at or near an extreme value of the penalty function. The extreme value may be a minimum value, for example. Assigning the value to each of said design parameters is not limited to using the penalty function to do so. Said instructions may further effect recording said assigned parameter values in a data structure on a computer-readable medium. The article may further include instructions which, when executed, operate a computer-aided manufacturing system in accordance with said values in said data structure, to manufacture said at least one of first and second components.

According to a seventeenth aspect, an article comprises a computer-readable signal, recorded on a computer-readable medium, and comprising instructions which, when executed, cause a computer system to perform a method of designing an optimized dental restoration component, comprising: receiving a set of design dimensional constraints which must be satisfied for the component; receiving a set of design parameters for the component; assigning a value to each of said design parameters, consistent with the constraints for said component; determining whether there is a conflict between possible values for a design parameter and the dimensional constraints for the component and, if there is a conflict, changing a value of at least one design parameter for the component and re-determining whether there is a conflict, until no conflict exists or it is established that for all values of the design parameters for the component there will be conflict; repeating the previous operation until values have been assigned to all design parameters of the component and no constraint or parameter value conflicts exist; and executing a penalty function to calculate an acceptable set of design parameter values for the component. The article may further include instructions which, when executed, operate a computer-aided manufacturing system in accordance with said acceptable set of values to manufacture said component.

According to a eighteenth aspect, there is discussed an article comprising a computer-readable signal, recorded on a computer-readable medium, and comprising instructions which, when executed, cause a computer system to perform a method of specifying a least one common design feature for at least first and second dental restoration components that must be installed in a cooperating relationship, said method comprising: receiving a set of design dimensional constraints which must be satisfied for each of the first and second dental restoration components; receiving a set of design parameters for each of the first and second dental restoration components; and assigning values to the common design feature for said first and second dental components such that there is an absence of conflicts between the design parameters and the design constraints of said components. The first and second components may comprise an abutment and a crown, and the at least one common design feature is a common margin for the abutment and crown.

According to a nineteenth aspect, a dental restoration abutment and a corresponding, paired dental restoration crown are provided, which when assembled together share between them a common margin, made any other processes noted above and suitable for the purpose. Similarly, a single dental restoration component made using any of the foregoing processes is intended as part of this invention.

Other aspects will become apparent from the detailed description which follows. In addition, it will be understood that the elements listed above and disclosed in the detailed description may be assembled in other combinations.

DETAILED DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
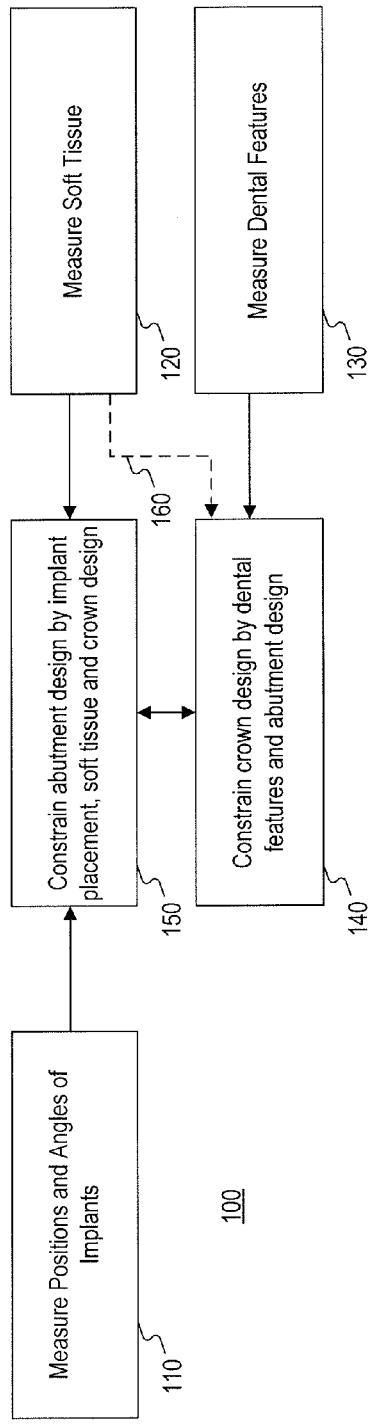
FIG. 1 is a high-level conceptual block diagram of a first example of an implant restoration design process as taught herein, wherein as a predicate, the required implant(s) has(have) already been fixed (i.e., placed) in the patient's jaw.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In connection with methods, use of the word "step" is not intended to invoke the construction specified in 35 U.S.C. §112, sixth paragraph unless a "step for" performing a function is recited in a claim.

Glossary

A large number of terms are used herein, and it may prove helpful to provide some guidance in their interpretation. Many of these terms may best be understood by reference to the accompanying drawing figures, as they relate measurements of dental features. In general, these definitions are not meant to be precise, and are offered only to give a general understanding of the intent, precise definition not be a requirement for understanding the invention. Thus, as used herein, the following terms have the meanings or properties herein ascribed to them.

"Abutment height" is the distance from the implant-abutment interface to the top of the abutment "Angulation" or "inclination" refers to the tilt of the long axis of a tooth in a mesial/distal or facial/lingual direction.

The "base" or "emergence profile region" is a zone from the implant interface to the margin, which interfaces with the soft tissue around a tooth or implant.

The "core" is the central portion of an abutment above the margin or gum line.

The "core region" is the zone from the margin to the top of the abutment, which interfaces with the restoration (i.e., crown or bridge).

"Core angle" is the direction of the abutment core.

"Core height" is the abutment height less average margin height.

The "counterbore" is a hole in the occlusal portion of abutment that provides access for the retaining screw.

The "crown" is the portion of a tooth or tooth restoration above the margin and, in the case of a restoration, is the final restorative component, typically fabricated in ceramic, metal or a combination of metal and ceramic.

"Distance to crown model" is defined at multiple locations at the height of the contact points. It defines the space available for the coping and porcelain of the crown and is determined by subtracting the core width from the width of the crown model.

"Edentulous" means without teeth. Edentulous space is a space where teeth are missing.

The "emergence profile" of a restoration is the shape of the abutment as it transitions from the implant to the margin—normally located within the soft tissue. "Emergence profile angle" is determined by margin widths and heights and is a single angle (at any margin section) not including the transitions from the implant interface and to the margin. The maximum angle of the emergence profile must be within a case specific limit. The emergence profile angle should point to the contact points as defined by the crown model. Emergence profile angles may be approximated by taking the arctangent of the ratio of adjusted margin height to adjusted margin width. The target emergence profile angles are equal to the angles of the crown model at the margin heights in each of the specified directions. Limit emergence profile angles may be set by the cone angle limits that depend on the case specific clinician preferences and will be provide as a scalar.

A "fixture" is a synonym for a dental implant. A fixture, or implant, is mounted in the maxillary or mandibular bone structure, and used as a base to mount a dental abutment.

The "margin" is the locus of the outer edge of the joint between abutment and crown.

"Margin heights" are measured in multiple locations about a restoration, in the base region, from the level of the implant along the Path Of Insertion.

"Margin widths" are measured in multiple locations about a restoration, in the base region, from the center of the abutment core to the margin. Margin widths interact with the counterbore (and implant axis) since the counterbore must be contained within the margins and should be contained within the core.

A "model" is a representation of an actual component, e.g. an abutment model or crown model.

"Occlusal clearance" is the distance to the opposing tooth (or teeth). It is defined differently for anterior and posterior teeth, and defines the space available for the coping and porcelain of the crown.

The "papilla" is the rise in soft tissue in the interproximal (i.e., between adjacent teeth) region.

The "Path of Insertion" (POI) is an imaginary direction along which the restoration will be placed onto or removed from the abutment (or prepared tooth) . . . Features of the abutment must permit the restoration to be placed along the POI.

A "pontic" is a tooth (or teeth) in a bridge that is(are) not supported by an abutment (implant abutment or prepared tooth).

A "restoration" is a structure creating a complete prosthetic tooth (e.g., implant, abutment, and crown)

The "shoulder" of a restoration is the area between the abutment margin edge, at the end of the emergence profile, and the core. Shoulder widths are measured in multiple locations and are the distance from the margin to the core. Shoulder widths define the restoration thicknesses at the margin. Facial widths are most critical, the interproximal widths are next in importance and the lingual widths are the least important. Shoulder widths interact with margin widths to affect core widths.

The "soft tissue," in the mouth, refers to the gingival, or gum, tissue

A "soft tissue model" is a flexible model of the gingival (gum) tissue that is separate from a study cast "Subgingival depth" is the distance of the margin height below the soft tissue (gum).

"Taper" refers to the reduction of the core above the margin of the abutment to allow placement of the restoration. Taper angle is the reduction in core width as a function of core height, measured from the core axis. The amount of taper affects retention—the smaller the taper angle, the greater the retention.

Overview

Among others references, U.S. Pat. Nos. 5,674,069, 5,989,029 and 6,231,342 teach computer-aided approaches to the design and fabrication of abutments for dental restorations. The process of designing and implementing a dental restoration for an implant fixture requires that the crown (or bridge, etc.) be geometrically compatible with the supporting abutment. Typically, dental technicians exercise their acquired judgment to create acceptable abutment and crown designs. That is, even when custom abutment and crown are produced by a computer-aided design and manufacturing (CAD/CAM) process, a dental technician still has to use craftsmanship. As more fully discussed below, it is possible to create an anatomically correct and geometrically compatible design for the abutment and crown, implementable by a computer-aided manufacturing system, by incorporating into that system appropriate design rules and algorithms, coupled with measurements of the edentulous space and surrounding teeth.

If abutment considerations were not included, the crown size and shape would be defined solely by the type of the tooth being replaced and by surrounding dental anatomy. However, crowns designed this way may require abutment geometry that is not consistent with limitations such as the angulation limit between the abutment and implant, abutment angle between the implant the margin, crown thickness, retaining screw counterbore location or manufacturing considerations. By providing a system for limiting the size and placement of crown designs, and the geometries that are consistent with realizable abutment designs, one can obtain compatible designs for the abutment and crown, or combined abutment-crowns, capable of implementation by computer-aided manufacturing equipment. This results in less expense manufacturing such components and it should reduce the number of visits by the patient to the dentist's office.

Constraints

Two situations will now be discussed. In the first, implant placement is treated as known and in the second, implant placement has not been established and is therefore to be specified by the design process. In the latter situation, two sub-cases present themselves. First, there may be a desired crown(s) or bridge design configuration the patient or clinician (e.g., dentist) wishes to accommodate, and the rest of the restoration (e.g., implant, abutment and possibly coping) are to be designed consistent with the constraints imposed by the known crown(s) or bridge. Second, the crown(s) or bridge may be specified (i.e., designed) as part of the process, along with the other components.

Turning to FIG. 1, a process 100 is outlined schematically for use in the circumstance that implant placement has already been determined. In act 110, the positions and angles of the implants are measured and input to a computer-maintained database (not shown). In act 120, appropriate measurements are made of the soft tissue in the implant's space. These measurements may include, for example, the location of the surface of the soft tissue, adjacent teeth and opposing teeth. In act 130 (sometimes referred to as Dentition Feature Detection (DFD), dental features are measured, such as the locations of contact points of adjacent teeth, the location of the surface of the opposing tooth (i.e., in the opposite jaw bone), or the locations of opposing tooth cusps and fossa; the locations of the facial and lingual dimensions of adjacent teeth and/or contra-lateral tooth; and the shape of the dental arch near the missing tooth or teeth. These features are used in act 140 to constrain the crown design, taking into account the abutment design. Based on those constraints and the measured positions and angles of the implants and soft tissue measurements, in act 150, the abutment design is constrained. Thus, a compatible crown and abutment design result, satisfying all constraints. Consequently, using the constraints, the range limits for acceptable crown size, location and orientation are first determined and it is then assured that the abutment design will be compatible with the crown design and that both will be within the limits of the design constraints.

The various measurements, or any of them, may be made manually or in an automated or semi-automated fashion. A system and method such as those shown in U.S. patent application Ser. No. 11/184,396, titled "REGISTRATION OF 3D IMAGING OF 3D OBJECTS", are hereby incorporated by reference, may be advantageously employed to obtain some of the measurements.

Note that, as explained more fully below, the approach shown in FIG. 1 may be modified. For example, one type of implementation discussed below employs a common margin for an abutment and a crown in a restoration. In that situation, the soft tissue measurements are also an input to the crown modeling process as well as to the abutment modeling process. Such an alternative is represented by dashed line 160. Other variants will be apparent to those skilled in the art.

Figure 2:
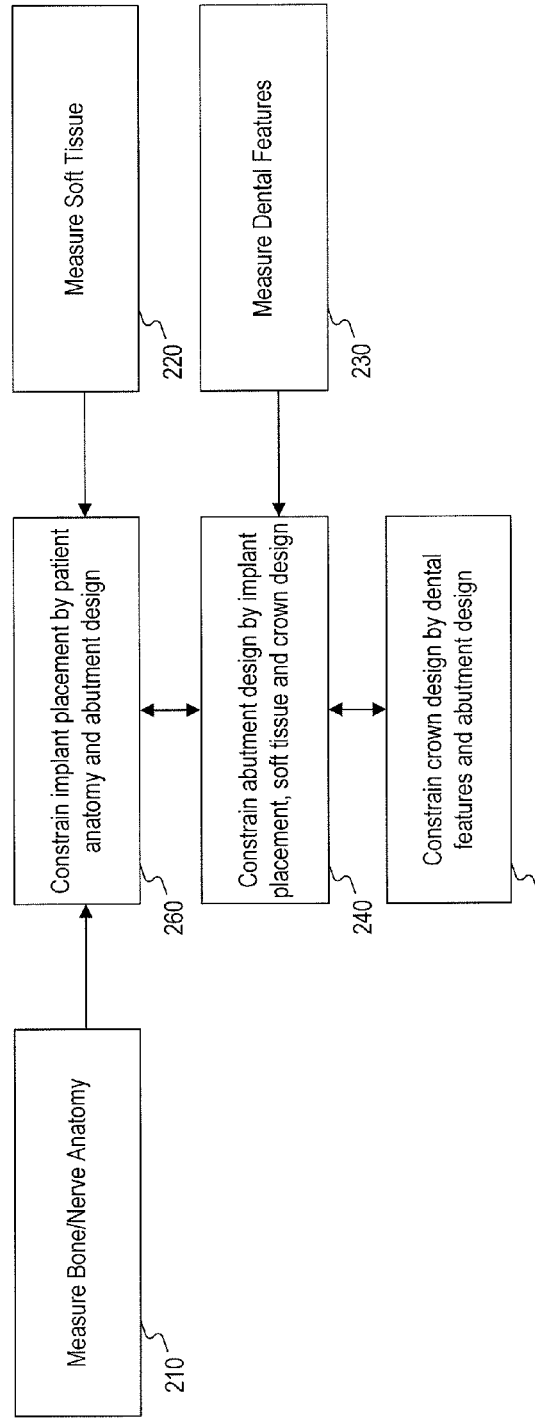
FIG. 2 is a high-level conceptual block diagram of a second example of an implant restoration design process as taught herein, wherein the implant(s) has(have) not already been fixed (i.e., placed) in the patient's jaw and the design of implant placement is part of such restoration process.

In contrast to the situation addressed with the method of FIG. 1, if the dental implant is only being planned and has not yet been implanted, the foregoing technique can be extended to constraining permissible implant placement location and orientation, along with the other components. This is illustrated in FIG. 2, for example. As shown there, appropriate features of the bone and nerve anatomy are measured in step 210. In step 220, soft tissue measurements are made and in step 230, dental features are measured. The abutment design is constrained interactively in step 240 with crown design, soft tissue features, implant placement and orientation constraints. Crown design is constrained interactively in step 250 with dental features and abutment design; and implant placement is constrained interactively with patient anatomy and abutment design in step 260. The simultaneous solution of all of the constraints yields an available range for each of the parameters for implant placement, abutment design, and crown design.

To select a specific value for each parameter, any suitable algorithm may be employed. For example, a midpoint value in the range may be selected for each parameter.

At least some of the measurements required for implant planning are typically made non-invasively using techniques such as computer-aided tomography, which are well known to practitioners of implant planning. Software tools such as SimPlant from Materialise NV may be used for visualizing bone measurement and implant placement.

The input from abutment design act (or step) or module 240 limits the range available for implant placement to that in which a realizable abutment and crown can be created. This may assist clinicians in determining when bone augmentation techniques are required to provide adequate implants support. That is, instead of initially placing implants without regard to their placement impact on abutments and crowns, abutments and crowns constrain the feasible range of implant placement.

In some situations, crown or bridge design may be pre-defined, and the task is then to design and locate the abutment and implant. For example, there may be a specific crown appearance the patient or dentist desires, assuming it can be obtained without violating a firm constraint. One way to obtain the three-dimensional measurements of the crown, needed for this process, is to create a false tooth or teeth of a radio-opaque or partially-opaque material, take one or more X-ray images and measure features off of the images. Alternatively, the crown may either be scanned optically and measurements taken from the scanned image, or it may be created using dental CAD technology.

Manifestly, the feasibility of a restoration plan including directions for implant placement also depends critically on the implant being placed in the patient's jaw in the planned location and orientation (in three dimensions). To facilitate placement of the implant, the dental surgeon may employ a template (also called a guide) for computer-guided surgery. The guide assists the drilling and placement of an implant fixture, based on the implant placement specified by the above processes. Such templates are well known and available from sources such as Materialise NV, which produces the SurgiGuide drill guides. It is recommended, though not required, that such a template be used when an implant is to be manually placed as part of a restoration plan not based on an already-placed implant. However, robotic surgery to insert an implant is available and does not require a template.

The following is a sample list of constraints that might be employed, though innumerable other sets of constraints may be established:

1. The maximum angle between the abutment core and the implant axes;
2. The maximum emergence profile angle;
3. The minimum shoulder width;
4. The minimum wall thickness for the abutment;
5. The minimum height for the abutment core;
6. The subgingival margin depth.

Along with applying these constraints, the following trade-offs may be used: Larger abutment margin widths allow wider shoulder widths and larger core wall thickness. Unfortunately, for thin soft tissue cases the abutments cannot have sufficient margin widths, because either the emergence profile angle will be too high or the subgingival depth will be insufficient. Other times, there is not sufficient room between the teeth for a wide abutment. This means that there is a trade-off of these parameters—forcing narrower margin widths (as subsequently narrower shoulder widths and/or thinner core walls) and/or margins that are not as subgingival as desired.

Another trade-off occurs because of desired core height to help retain the cemented crown. Sometimes the opposing tooth is too close, forcing a shorter core. In other circumstances, small margin width coupled with a required taper angle limits the abutment height as the taper approaches the counterbore.

Solving the Constraint Interactions

Steps 140, 150, 240, 250 and 260 express the concept that various constraints are inter-dependent. They do not indicate how those interdependencies are solved to achieve a set of parameter values that satisfy all of the constraints. In fact, there are multiple ways and sequences one may go about defining the ranges of parameter values that are acceptable, and of choosing a final set of values within that overall solution space. In general, for example, iteration techniques will allow variables to be constrained, so that the variable values are bounded in a consistent and non-conflicting way. One may choose to focus first on the abutment, for example, and use the selection of abutment parameter values to further constrain the crown. If a conflict is reached, meaning that the crown design cannot be completed, then the process loops back to the abutment design, changes the abutment parameters, and tries the crown again. Assuming that there does exist a permissible solution for both the abutment and crown, this approach will find it. A thus structured approach permits a retracing of steps and moving forward to a new solution if a conflict in constraints is encountered, until such conflict no longer exists.

One also may choose the crown as the starting point, solve for the crown parameters, and then move on to the abutment, looping back to the crown only when the abutment design cannot be completed.

Optimization

Another approach is to use optimization methods, which permit a simultaneous solution to be found for a group of variables in a multivariable system, and to assure this solution is a highly satisfactory solution. This approach is explained more fully below.

Multi-dimensional (also called multi-parameter or multi-variable) designs can be optimized using a suitable performance metric (also known as a functional, or penalty function) that can be minimized (or maximized). Various metrics are known in the field of optimization, or can be readily created. It is not intended, except as required by specific claims, that the invention be limited to use of a particular set of parameters (defining implant, abutment and crown or bridge characteristics, or interrelationships) to be optimized or that the invention be limited to one particular performance metric—or some select set of metrics—for processing to obtain optimal values. Any appropriate metric(s) may be employed and optimized (i.e., minimized or maximized), within the limits imposed by the set of selected constraints.

Although those skilled in optimization techniques will have no difficulty in designing appropriate penalty functions, some guidelines and examples may facilitate the effort. The penalty function may (and preferably does) have the most or all of the following properties: penalty values are continuous and increase monotonically away from a center value; at the center value, the penalty value is minimum and near zero, as is its first derivative; the penalty value has a continuously and monotonically increasing first derivative (decreasing for negative deviations), within the range of interest; at specified values of the variable, both above and below the center value, the penalty function has a value of unity and a controlled first derivative; at predetermined limit values for the variable, both above and below the center value, the penalty function has specified penalty values and specified first derivatives; it also has specified slopes beyond the limit values (equal to the first derivatives at the limit values).

It may be useful, for computational purposes, to divide the penalty function into a number of segments. For example, one possible penalty function for abutment design may divide the parameter range into six segments—three above nominal value for the variable (center value) and three below the center value. The computation of the penalty function may be different in each segment.

The same form of penalty function can be used for all variables with only minor limitations. The variable may be centered by subtracting the center value from the variable. Variables may be normalized separately for positive and negative deviations from the center value by dividing the centered variable by its value when the penalty function is equal to unity.

The following is one example of a general process may be used in creating penalty functions, though deviations from this recipe are certainly expected and intended:

1. Start with a weight of unity;
2. Make the penalty function zero when the parameter is at the desired level;
3. Make the penalty function unity when the parameter is at a marginally acceptable level;
4. Make the penalty function very high (e.g., 100) when a hard constraint (i.e., limit) is exceeded;
5. Adjust the weights to provide emphasis of one parameter over another (or others);
6. Try the system in a range of cases to see where it works and where changes are required;
7. Use tooth number, clinician preference, dental context (e.g. facial or lingual placement, narrow of wide edentulous space, etc.) or like factor(s) to adjust weights.

A first example of an implementation of a penalty function will now be provided.

Considering only positive deviations from a center value, define three regions, Regions A, B and C, for a normalized and centered variable, $\overline{X}$:

Region A: $0 \leq \overline{X} < 1$,
Region B: $1 \leq \overline{X} < \overline{XL}$, where $\overline{XL}$ is the centered and normalized limit value
Region C: $\overline{XL} \leq \overline{X}$ The penalty function y is defined separately for each region:
Region A: $y_1 = \overline{X}^n$, where n is typically 2, and $$n < \frac{YL-1}{\overline{XL}-1},$$

where YL is the penalty value at $\overline{XL}$. Note: the derivative at $\overline{X}=1$ is n, and the projection to $\overline{XL}$ must be less than YL.

Region B: $y_2 = 1 + n*(\overline{X}-1) + a_2*(\overline{X}-1)^m$, where $$m = \frac{(SL-n)*(\overline{XL}-1)}{YL-1-n*(\overline{XL}-1)},$$

and $$a_2 = \frac{SL-n}{m*(\overline{XL}-1)^{m-1}}.$$

Region C: $y_3$ may be an arbitrarily steep function, possibly reaching a predetermined limit.

Figure 3:
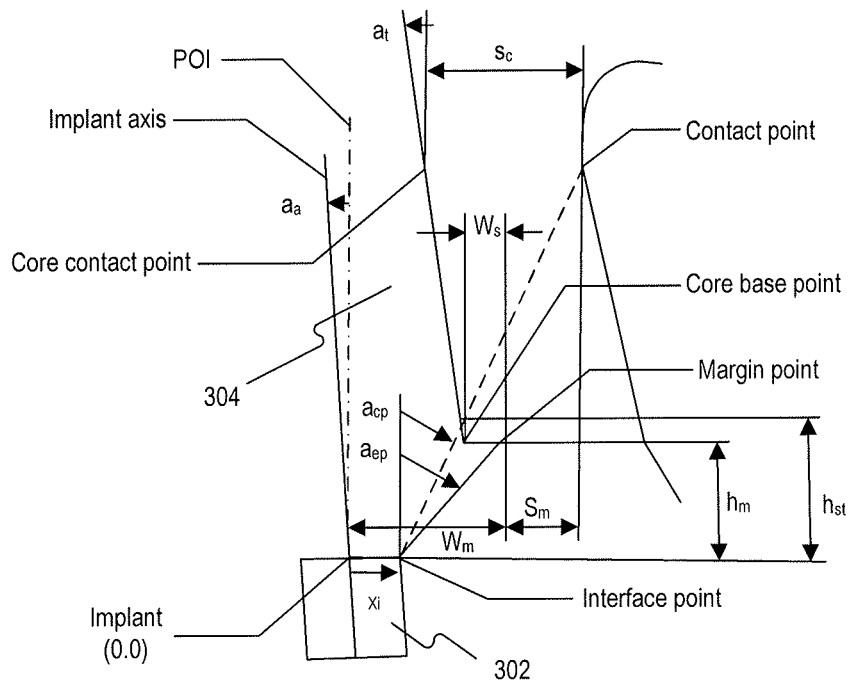
FIG. 3 is a diagrammatic illustration, from a single side view, of an implant and an abutment showing several design parameters.

Table II, below, shows the corresponding values for the above variables, for one example wherein the parameter to be optimized is a facial shoulder width. Reference may be made to FIG. 3 for a drawing illustrating an exemplary set of measurements for an implant 302 and abutment 304 (only one half of which, truncated, is shown). The reader should appreciate that this set of measurements and this illustration are not meant to define all dental situations or systems for practicing the invention. For example, if a differently shaped abutment base were employed, appropriate modifications would be required, and these modifications would be apparent to clinicians and engineers.

TABLE II

Facial Shoulder Widths

|  | Values | Centered Values | Normalized and Centered Values | Calculated Values |
|---|---|---|---|---|
| Zero Value | 1.2 | 0.0 | 0.0 |  |
| Unity Value+ | 1.6 | 0.4 | 1.0 |  |
| Limit Value+ | 2.0 | 0.8 | 2.0 |  |
| Penalty at + Limit | 4 |  |  |  |
| (YL − 1)/($\overline{XL}$ − 1) |  |  |  | 3 |
| N | 2 |  |  |  |
| SL | 100 |  |  |  |
| M |  |  |  | 98 |
| $a_2$ |  |  |  | 1 |
| Unity Value− | 0.8 | −0.4 | 1.0* |  |
| Limit Value− | 0.5 | −0.7 | 1.75* |  |
| Penalty at − Limit | 3 |  |  |  |
| (YL − 1)/($\overline{XL}$ − 1) |  |  |  | 2.667 |
| N | 2 |  |  |  |
| SL | 100 |  |  |  |
| M |  |  |  | 98 |
| $a_2$ |  |  |  | 1 |
| Weight | 2 |  |  |  |

*negative deviations are modeled the same as positive deviations

Figure 4:
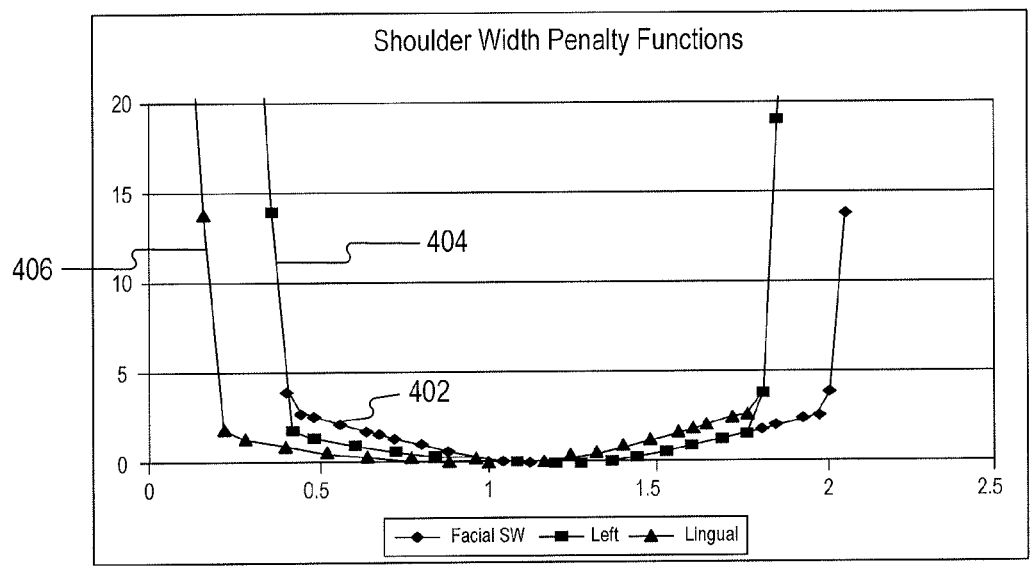
FIG. 4 is a graph of three exemplary shoulder width penalty functions, non-normalized.
Figure 5:
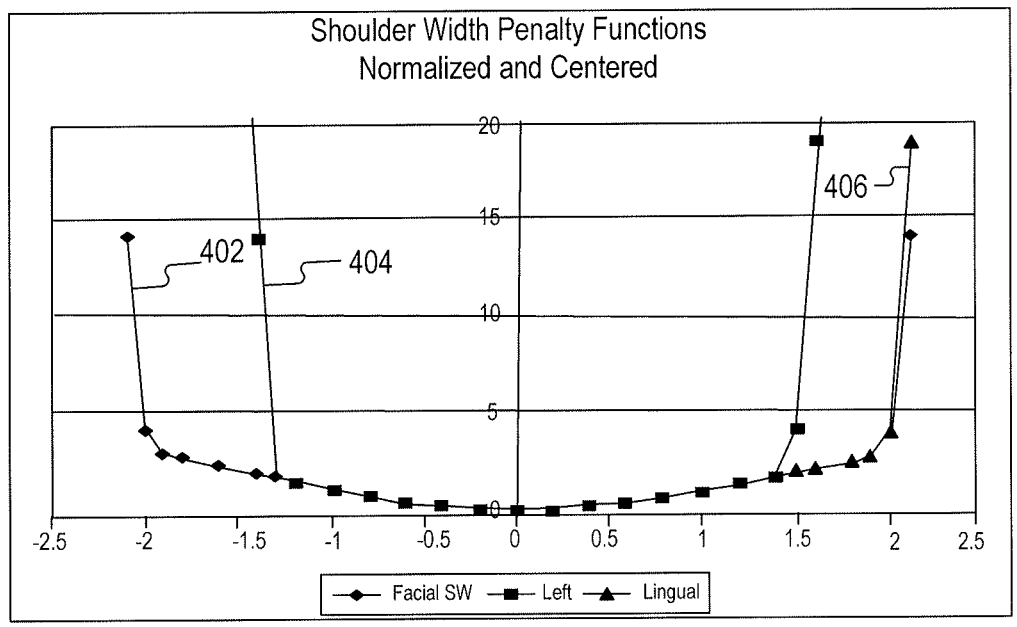
FIG. 5 is a graph of the same three exemplary shoulder width penalty functions, centered and normalized.

Corresponding graphs 402, 404, 406 of the non-normalized penalty functions for (respectively, exemplary facial, left and lingual) shoulder widths are provided in FIG. 4; and corresponding graphs 412, 414, 416 of the normalized and centered penalty functions for the same shoulder widths are shown in FIG. 5.

More generally, a commonly used form for a penalty function is:

$$PF = \sum_i w_i * (p_i - p_i^o)^2 + \sum_n \lambda_n,$$

where

PF is the penalty function to be minimized, $w_i$ is the weight to be applied to the $i^{th}$ parameter, $p_i$ is the $i^{th}$ parameter, $p_i^o$ is the nominal value of the $i^{th}$ parameter, and $\lambda_n$ is the $n^{th}$ optional parameter.

Of course, other forms can be used (such as other powers, transcendental functions and piecewise linear functions), since all share the general intent of a penalty that monotonically increases as the parameter deviates from the desired value. Although in the above examples, the penalty function is symmetrical about a center (i.e., relative to the deviations from the target), a penalty function also can be made asymmetric. The general form for the penalty function forces the parameter to the desired value unless other parameters are forcing it away. If a common form of penalty function is used for all parameters, the relationship between weights provides the differential emphasis between parameters. Absolute values for the weights are not important since the value of the penalty function simply scales with the absolute size of the weights. The weights can be changed with conditions or additional weights can be applied for specific conditions, e.g. $w_i = w_i' * w_i'' * w_i'''$.

Figure 6:
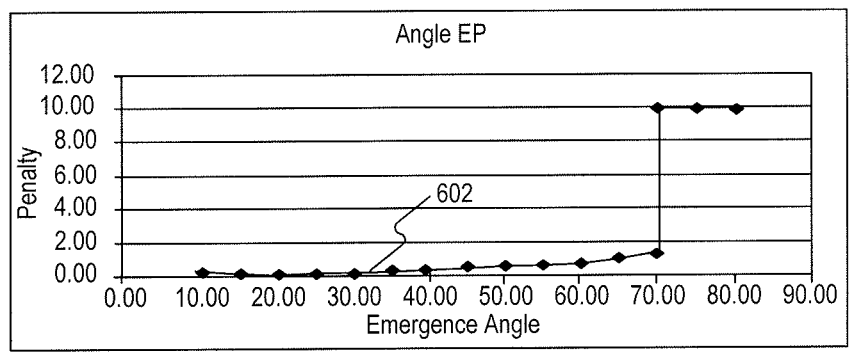
FIG. 6 is a graph of an example of an emergence angle penalty function.
Figure 7:
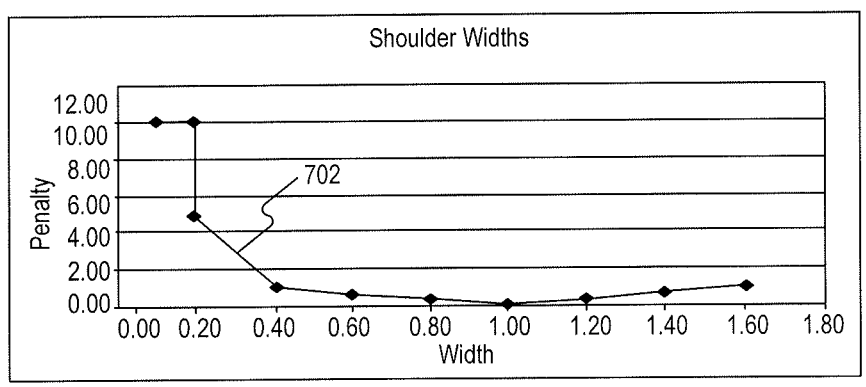
FIG. 7 is a graph of an example of a shoulder width penalty function used in conjunction with the graph of FIG. 6 to demonstrate penalty function-constraint interaction.

Referring to FIGS. 3, 6 and 7, there is illustrated another example of optimization, this one limited to the interproximal region. It is intended to demonstrate the potential of optimizing abutment width and shoulder width. Margin subgingival depth, another important parameter, is held constant during this optimization so that the performance metric can be displayed in a two-dimensional array. The following relationships and limits are intended to be consistent with a set of proven abutment design rules. The list is not exhaustive, only illustrative:

Relationships

Interface point: $p_i = (x_i, y_i) = (r_i * \cos(a_a), r_i * \sin(a_a))$

Margin point: $p_m = (w_m, h_m)$

Core base point: $p_{bp} = (w_m - w_s, h_m)$

Contact point: $p_{cp} = (x_{cp}, y_{cp})$

Core contact point: $p_{ccp} = (w_m - w_s - (y_{cp} - h_m)\tan(a_t), y_{cp})$

Emergence profile angle: $a_{ep} = \tan^{-1}((w_m - x_i)/(h_m - y_i))$

Contact point angle: $a_{cp} = \tan^{-1}((x_{cp} - x_i)/(y_{cp} - y_i))$

Limits

Space from core to adjacent tooth (at contact point): $\min_{sc} < s_c < \max_{sc} s_c = x_{cp} - (w_m - w_s - (y_{cp} - h_m)\tan(a_t))$ Space from margin point to adjacent tooth (cp): $\min_{sm} < s_m < \max_{sm} s_m = x_{cp} - w_m$ $s_c$ and $s_m$ are not independent—affected mainly by $w_s$ and $a_t$: $s_c - s_m = w_s + (y_{cp} - h_m)\tan(a_t)$ Emergence profile angle is below the limited angle $a_{ep} < a_{limit(1)}$ The shoulder width is within acceptable limits $w_s > 0.2$ mm, preferably $> 0.4$ mm $w_s < 1.4$ mm At the margin, the core thickness is above the minimum value $w_m - w_s > r_{cbore} - h_m * \sin(a_a) + 0.2$ mm.

Figure 8:
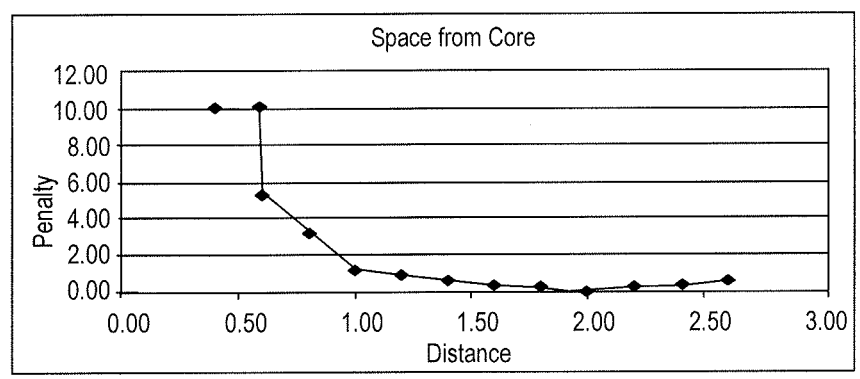
FIG. 8 is a graph of an example of a space-from-core penalty function discussed in relation to the penalty functions of FIGS. 6 and 7.

The examples of three penalty functions illustrated in FIGS. 6-8 (a fourth is not shown as it is similar to the 'Space from Core' function 802 except that its distance parameter is 0.5 mm less than the 'Space from Core' function) for a hypothetical patient demonstrate the optimization for two parameters, shoulder width and margin width. The penalty function 602 for an emergence profile angle is zero when the emergence angle is equal to the angle that points from the edge of the implant interface to the contact point (~21 deg. for this example), and has a value of approximately unity when it is 70 degrees (arbitrary limit for this example), then 10 above 70 degrees. A maximum value of 10 was used to limit the display range. The penalty function 702 for shoulder width is zero at 1 mm. It increases to unity at a width of 0.4 mm; then increases more rapidly until it reaches the limit at 0.2 mm. This could have been implemented as a changeable limit, with an initial limit at 0.4 mm, for example. The penalty function 802 for spacing from the core to the contact point is zero at the desired value of 2 mm and increases rapidly below a distance of 1 mm when the penalty is unity. The limit is 0.6 mm.

The inputs to this optimization process typically include: implant interface diameter, counterbore diameter, contact point location, soft tissue height, subgingival depth, and taper angle.

A more complete optimization might also include a penalty function for core wall thickness.

Although we have presented a number of penalty functions for individual parameters, and single parameter optimizations, this is not sufficient to permit design and fabrication of components that together will satisfy a collection of constraints that require interactivity in the design process. Were either the abutment or the crown designed without regard to constraints imposed by the other component, it is fairly likely the two components would not fit together properly and would not meet the overall situational constraints. The next need is to "combine" the individual penalty functions into one overall optimization process, taking into account the constraints imposed by the environment and materials (e.g., minimum thicknesses). This may be achieved in a number of ways, including creating an overall, multi-variable penalty function for the restoration project, such that the overall penalty function can be minimized or maximized (as the case may be) once the limits (constraints) are known for each variable. One possible total penalty function (equally weighting the variables) is the sum of the penalty functions for the individual parameters, such as emergence angle, shoulder width, space from core and space from margin.

Using the individual penalty functions of FIGS. 6-8 and other data (not shown), one may see a typical variation in the penalty function with shoulder width and margin width, in Table III.

TABLE III

|  |  | Shoulder Width | | | | | | | | | |
|---|---|---|---|---|---|---|---|---|---|---|---|
|  | 1.69 | 0.25 | 0.50 | 0.75 | 1.00 | 1.25 | 1.50 | 1.75 | 2.00 | 2.25 | 2.50 |
| Margin | 2.25 | 17.8 | 14.6 | 14.3 | 13.9 | 14.3 | 14.6 | 17.8 | 23.9 | 23.9 | 23.9 |
| Width | 2.50 | 8.0 | 12.0 | 11.6 | 11.3 | 11.6 | 12.0 | 15.2 | 21.3 | 21.3 | 21.3 |
|  | 2.75 | 6.1 | 4.7 | 11.4 | 11.0 | 11.4 | 11.8 | 14.9 | 21.0 | 21.0 | 21.0 |
|  | 3.00 | 5.4 | 2.6 | 4.0 | 10.8 | 11.1 | 11.5 | 14.7 | 20.8 | 20.8 | 20.8 |
|  | 3.25 | 5.0 | 2.2 | 2.2 | 3.5 | 11.0 | 11.4 | 14.6 | 20.7 | 20.7 | 20.7 |
|  | 3.50 | 4.6 | 1.7 | 1.7 | 1.7 | 3.8 | 11.3 | 14.4 | 20.5 | 20.5 | 20.5 |
|  | 3.75 | 4.9 | 1.8 | 1.7 | 1.6 | 2.4 | 4.5 | 14.8 | 20.9 | 20.9 | 20.9 |
|  | 4.00 | 5.5 | 2.1 | 1.8 | 1.6 | 2.4 | 3.1 | 8.0 | 21.2 | 21.2 | 21.2 |
|  | 4.25 | 6.2 | 2.8 | 2.2 | 1.9 | 2.5 | 3.2 | 6.7 | 14.6 | 21.7 | 21.7 |
|  | 4.50 | 7.1 | 3.6 | 2.9 | 2.3 | 2.8 | 3.4 | 6.9 | 13.3 | 15.1 | 22.2 |
|  | 4.75 | 10.9 | 6.6 | 5.9 | 5.2 | 5.3 | 5.8 | 9.2 | 15.6 | 16.0 | 17.7 |
|  | 5.00 | 19.7 | 14.1 | 12.6 | 11.8 | 11.9 | 12.0 | 15.3 | 21.6 | 22.0 | 22.3 |
|  | 5.25 | 25.2 | 16.7 | 13.8 | 12.3 | 12.3 | 12.4 | 15.3 | 21.5 | 21.7 | 22.0 |
|  | 5.50 | 25.3 | 22.1 | 16.4 | 13.5 | 12.8 | 12.8 | 15.6 | 21.5 | 21.6 | 21.8 |
|  | 5.75 | 25.4 | 22.2 | 21.8 | 16.1 | 14.0 | 13.2 | 16.0 | 21.8 | 21.5 | 21.6 |
|  | 6.00 | 25.4 | 22.3 | 21.9 | 21.5 | 16.5 | 14.4 | 16.4 | 22.2 | 21.9 | 21.6 |

Note that the optimal region occurs with a shoulder width of 1.0 mm, but the design is relatively insensitive within the region running from a shoulder width of 0.5 and margin width of 3.5, along a diagonal to a shoulder width of 1.0 and margin width of 4.0.

Changes in location of the contact point, tissue height or desired subgingival depth will have significant influence on the design tradeoffs.

Thus, to use a penalty function(s) to obtain a set of design parameters, one generally has to seed the penalty function weights and then employ an iterative solution approach to reach a final set of values. An educated guess may be used as a good starting point for the parameters. Many of the weights and forms for "penalty functions" then can be fine tuned by observing the effects on component designs. That is, an implementation preferably initiates the design near the optimum, then "guides" the modeler so that modifications either improve the design (through changes in the plan) or at least enable change to remain within an acceptable range, to produce a set of acceptable (optimal or near optimal) design parameter values.

Design Parameters

The number and selection of parameters for producing a suitable abutment and/or crown or abutment-crown is left to the designer. Without being exhaustive, some or all of the following parameters may be employed in an optimization process as above-described, to facilitate manufacture of customized dental restoration components: shoulder width; abutment wall thickness below margin (i.e., counterbore emergence); emergence cone angle (which may vary with clinical choice); blanching parameter (which also may vary with clinical choice); stretch parameter (also variable with clinical choice); margin subgingival depth (varies with clinician choice, tooth position and tooth surface); retention—a combination of core height, core width, taper angle and units in restoration; interproximal space from margin to adjacent tooth (or location relative to ideal crown); spacing from core to adjacent tooth; occlusal clearance (varies with tooth position); cusp alignment; occlusal edge parallelism; restoration size with respect to neighbors and contralateral; core taper angle with respect to other units in restoration; core wall section above the margin (moment of inertia in bending); and final emergence angle with respect to ideal crown profile.

In some situations, it may not be possible automatically to satisfy all of the constraints which have been input. In such situations, the system preferably detects the irresolvable conflicts and signals the clinician, such as on a computer screen. The clinician can then decide how to change the constraints in order to achieve a workable solution.

As an alternative to creating and minimizing an overall, multivariable penalty function, single variable or fewer-than-all variable penalty functions, or at least some of them, may be ordered individually or in groups, essentially creating a hierarchy of penalty functions. In this way, by controlling the sequence in which penalty functions are evaluated to define permissible ranges of values and optimal values for the involved parameters, optimization can be layered and prioritized.

As an example of the tradeoffs that may be involved, consider margin heights and margin widths. Initial estimates for margin heights and widths can be obtained from intersecting the crown model with the soft tissue model. Margin heights may be set by subtracting the subgingival depths from the obtained heights, if the obtained values are within limits set by constraints. If not, then the initial value can be set using the procedure described below. The subgingival depths may be provided in a vector with three values. Margin widths may be set at the width values obtained, if the obtained values are within limits set by the constraints. If not, then the initial value can be set using another procedure. For example, if the cone angle constraint is exceeded, the margin height may be increased by the subgingival depth. If the cone angle constraint is still exceeded, then the margin width may be decreased to set the cone angle to its constraint limit. If the counterbore limit is exceeded, the margin width is increased so that it is at the counterbore limit.

Copings

Up to this point, no mention has been made of copings. In restorative dentistry, there is often a fourth item present beyond the implant-abutment-crown trilogy. This additional element is called a coping. A coping (many designs for which appear in the literature and products) is a structure that provides an interface between the abutment and the crown, for reasons we need not elaborate. Specifications for minimum crown thickness at various points will, by simple arithmetic, constrain maximum coping dimensions. Other constraints may arise from material selections or other factors. It suffices to say, however, that when a coping is to be used, its design parameters (i.e., size and shape, interior and exterior) also need to be established.

The Design Platform

The above-described design processes preferably are performed on a computer or computers executing computer programs that carry out the necessary steps or acts. The measurement actions may be performed by making manual measurements and inputting the values via a keyboard or other input device, or they may be automated and the values may be electronically transferred into the computer(s). No specific measurement technique or system is assumed. When the expression "computer-implemented method" is used, the measurements, design parameters, constraints, and penalty function(s) may be considered as input to the method or generating, defining or providing such data may be considered as a part of the method. A computer system for designing or manufacturing dental restoration components may likewise receive such information as input data or the system may include the apparatus required to obtain the measurements, etc.

Manufacture

Following the optimization process, once the values for parameters defining each component have been established, those values may be recorded in an appropriate computer data structure in any suitable memory medium. Software which runs on the processor(s) of a computer-aided machining (CAM) system then uses those values (or a subset of them, at least) to manufacture the components. Suitable equipment for performing the machining operations will depend in large part on the selection of materials, but may include computer-controlled milling machines or other well-known techniques for creating 3-D shapes. This invention is not intended to be limited to any particular CAM equipment or methods.

The automated design of a coping deserves particular comment because its shape need not be closely related to the final tooth shape. Rather, it has to conform only to the interior of the crown and the exterior of the abutment. Coping manufacture can be approached in more than one way. One way to make a coping is to develop a model for the crown—i.e., its parameters—and to create as a derivative (coping) a component which has an outer contour matching the inner contour of the crown, for at least part of the height of the abutment. Similarly, once a model for the abutment is created, the outer contour of the abutment can be used to create the inner contour of a coping. Both approaches may be employed to form a coping that form fits to both the abutment and the crown. Adhesive (for example) may be used to attach the coping to the other components. The inner crown contour and outer abutment contour can be established with the foreknowledge that a coping will be used, allowing for a predetermined thickness of coping material, such thickness being subtracted from one or both of the abutment and crown, compared with the thickness they would have in the absence of a coping being used.

Crowns and bridges so made may be permanent or temporary.

The result of the foregoing processing is a data structure comprising a data file or files (stored on an appropriate computer-readable medium or media), representing an optimized set of components, which then can be manufactured with a CAM system. The entire design and manufacturing process can occur with minimum human labor, as the measurement process can be largely automated, also. The design quality and fit are high, and the cost of the restoration project is reduced.

In addition, the computer files defining the components can be used to drive 3-D printing and other rapid prototyping systems, if desired. 3-D printing and rapid prototyping are techniques that permit the technician, dentist and even the patient to see how the finished arrangement is going to look and fit together—before the actual dental components are made.

While these techniques can be used to make various kinds of arrangements, it should be noted, in particular, that screw-retained crown designs and integrated abutment-crown designs are specifically made possible. Making a unitary, combined abutment-crown structure avoids creating a potential for weakness at an abutment-crown interface, and reduces labor requirements. It also may facilitate manufacture of the unitary combination out of a ceramic material.

Planning

It should be apparent that the foregoing methodologies also lead to or enable a number of approaches to restoration planning.

Figure 9:
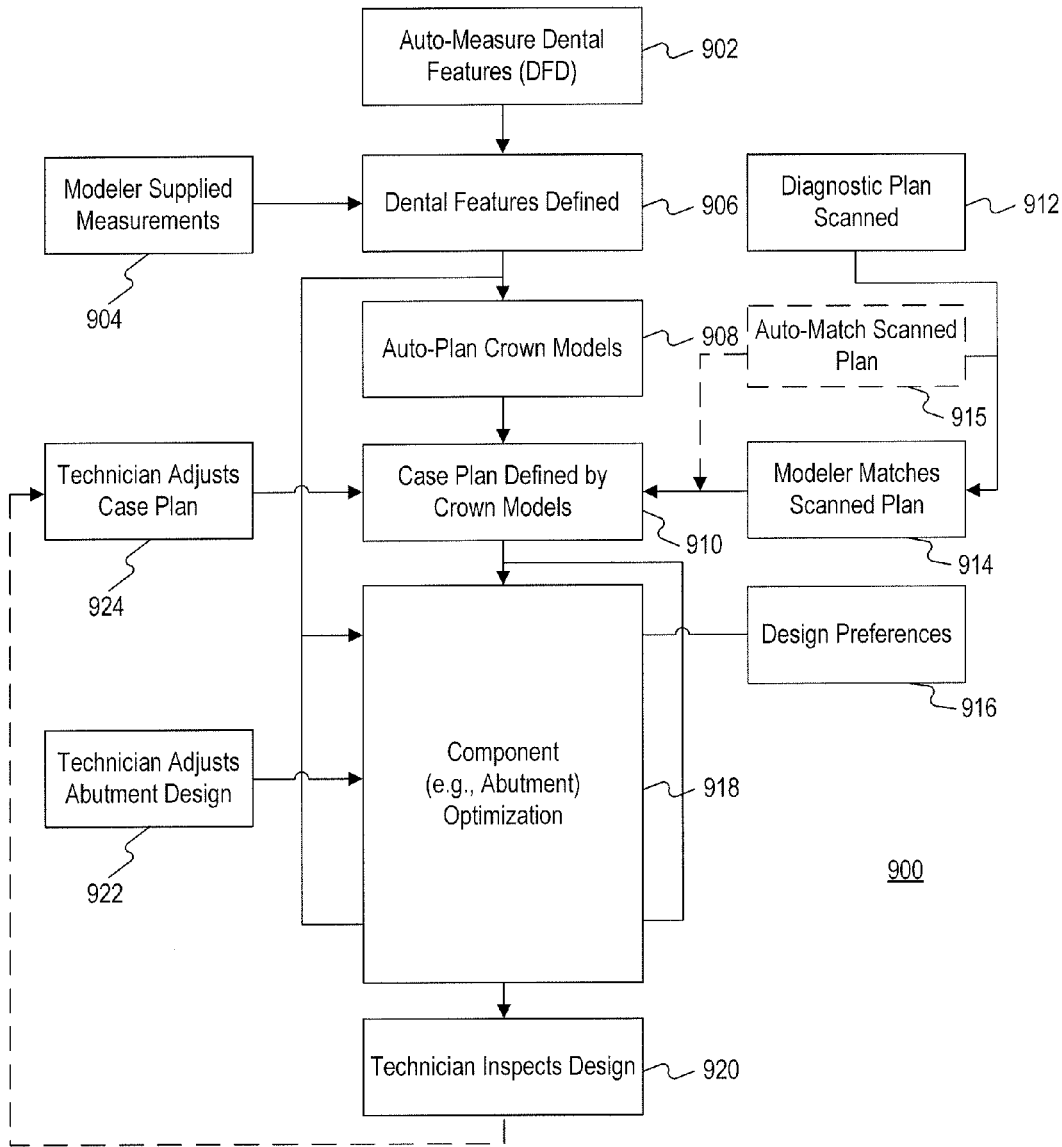
FIG. 9 is a part-flow, part-block diagram useful for understanding the overall restoration planning process in which aspects of the present invention may be utilized.

Turning to FIG. 9, there is shown, in general, a flow chart 900 for an example of the flow in a system for designing a single restoration component, such as an abutment, with "optimization" as taught herein. The intended crown design in this example is specified at the outset buy a technician or clinician. The term "optimization" is not meant to require that each of the component's design parameter values is the "best" or a perfect value, but that all constraints are satisfied and that the resulting design parameter values are at or near an overall preferred design point and that the design as a whole is therefore objectively acceptable and should be acceptable to the clinician.

Basic dental features are first measured, preferably in an automated or semi-automated system, at operation 902. Typically, these measurements are reviewed, selected and sometimes adjusted during a manual inspection conducted by a technician, operation 906. The technician may take into account measurements supplied by the clinician or his technician and indicated at 904. Using the set of dental features from operation 906, a software-assisted crown model plan may be formulated, in act 908. Such software is not part of the present invention and is typically customized computer-aided design (CAD) software that can be used to achieve a "first cut" at a design. The result of operation 908, taken together with a virtual crown model, is a so-called "case plan" 910, which is a representation of where the restoration teeth (crowns) are intended to be. The virtual crown model results from scanning a proposed (diagnostic) plan model prepared by a technician, Operation 912, and matching the scanned data with modeling information and dental feature data. Either a modeling technician (914) or software (915) can be employed to match the scanned plan to a computer model. The result of operation 914 or 915 is a "virtual" restoration plan—i.e., a computer representation of the physical plan model created by the technician and scanned in operation 912. Using the crown model(s) and design preference information 916 (i.e., design parameter values preferred by the clinician—however obtained—or employed as default values), the optimization processes described herein then may be used to design an abutment, Operation 918. A technician may inspect the resulting design, Operation 920, and, if necessary, adjustments may be made to the abutment design parameters or preferences (922) and/or the case plan (924). Then operation 918 may be repeated until the technician is satisfied.

As explained elsewhere, suitable modifications to the flow of FIG. 9 may be made when restoration components other than abutments are to be designed, or multiple components are to be designed. For example, if the crown design is an unknown, along with the abutment design, then the crown design is not an input to the process Different clinicians (e.g., restoration dentists and dental surgeons), experience shows, have different preferences for certain limits and penalty functions. For example, one clinician may be willing to accept a slightly smaller minimum margin than would another clinician. These clinician preferences may be specified by the clinician in response to a questionnaire, such as an on-line form; or they may be "learned" by the computer system as feedback is received on proposed designs. That is, as a clinician refers patients into the system and the system proposes restoration designs to the clinician, the clinician is given the opportunity to modify the design proposal and the computer system may record both the final parameters and the fact that the clinician modified the original proposal, and the nature of the modification. Using this information, the default parameters for future restorations for that particular clinician can be modified so that in the long run, it is likely that modifications will be minimized in number and degree. Ideally, the system learns the clinician's requirements and no modifications will even be requested most of the time.

As well, once a database of clinician preferences has been developed, it is possible to present to a first clinician not only the design her stored preferences would dictate, but also a number of other designs made using other clinicians' preference profiles. This allows a given clinician to consider alternative approaches or to seek design ideas if her own preferences lead to compromises she considers undesirable.

Thus, a database of clinician preferences (i.e., preference profiles) preferably is assembled in a computer storage unit and this database is used to establish at least some of the penalty functions and limits for some or all restoration projects for a clinician who is already profiled in the database.

Shared Abutment and Crown Parameters

A further aspect of the invention is that the abutment and crown models can be made to share a common margin. That is, their surfaces can be designed and manufactured, automatically, to be almost exactly congruent at the locus of contact. One way to achieve this result is to define the surface contour of the two components using a common set of points and parameters. If any point is moved or parameter changed in one model, the other model is automatically changed in precisely the same way. In other words, the two surfaces are forced to be congruent by definition. They will differ only by manufacturing tolerances.

Additionally, in some embodiments, the foregoing techniques and system may be used to inform a surgeon where to place an implant in order to achieve a realizable restoration. After the implant is placed, since that placement usually will deviate in some way from the plan, it may be measured and the remainder of the restoration may be designed and fabricated. Thus, the plan for the restoration may start with the selection of the crown design and work toward the implant placement that is optimized to permit use of such a crown. Or, alternatively, the plan may start with an implant that has been or will be placed by a surgeon, taking into account the patient's anatomy, and the abutment and crown design can follow, constrained by the already-placed implant. Either way, an optimal design can be provided.

Multiple Restorations

The same techniques discussed above in connection with restoring a single tooth can be employed in connection with restoring multiple teeth—i.e., designing and making or installing multiple implants, multiple abutments, multiple crowns and multiple integral combinations of abutments and crowns. For example, constraints may be provided to govern and enforce relationships between multiple abutments (such as keeping the abutment cores parallel), as well as to govern and enforce the relationship desired between multiple crowns (such as preventing them from overlapping).

Cross-component penalty functions also may be defined and used in an optimization process along with single-component or single tooth optimizations. Thus, a total optimization may be executed across a group of restoration components, to perform all of the trade-offs and satisfy all of the constraints that are imposed on a multi-unit restoration while simultaneously meeting the constraints on each component individually, to define a design that is acceptable and meets all requirements (assuming such a solution exists). Cross-tooth optimization allows the software, for example, to meet a required spacing between crowns by adjusting a first crown's dimensions or a second crown's dimensions, or both crowns' dimensions, while also satisfying the constraints placed on each crown individually. Thus, parameters to be optimized may include not only parameters for a single restoration, but also parameters specific to multiple-tooth restorations.

Computer Implementation

Many of the operations defined above, in the nature of measurement, data acquisition, data processing, database creation and usage, creation and use of penalty functions, and so forth, may be computer implemented or include computer-implemented acts or steps. Software and data can be stored on computer readable media and can be executed or accessed at a later date. Software can be used, for example, to obtain data, store data, organize data, correlate data and to provide information to a client. The software can be written in any computer language or languages and may run under any suitable operating system running on any suitable processor(s).

Some of the methods described herein and various embodiments and variations of the methods and constituent acts, individually or in combination, may be defined by computer-readable signals tangibly embodied on more computer-readable media, for example, non-volatile recording media, integrated circuit memory elements, or a combination thereof, as instructions for one or more processing elements. Computer readable media can be any available media that can be accessed by a computer. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can be accessed by a computer, and any suitable combination of the foregoing or replacement technologies therefor. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, wireless media such as acoustic, RF, infrared and other wireless media, other types of communication media, and any suitable combination of the foregoing.

Computer-readable signals embodied on one or more computer-readable media may define instructions, for example, as part of one or more programs, that, as a result of being executed by a computer, instruct the computer to perform one or more of the functions or operations described herein, and/or various embodiments, variations and combinations thereof. Such instructions may be written in any of a plurality of programming languages, for example, Java, Visual Basic, C, C#, or C++, Fortran, Pascal, Eiffel, Basic, COBOL, etc., or any of a variety of combinations thereof. The computer-readable media on which such instructions are embodied may reside on one or more of the components of any of systems described herein or known to those skilled in the art, may be distributed across one or more of such components, and may be in transition therebetween.

The computer-readable media may be transportable such that the instructions stored thereon can be loaded onto any computer system resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement the above-discussed aspects of the present invention. Any reference to a processor or to multiple processors is intended to encompass both the singular and the plural.

It should be appreciated that any single component or collection of multiple components of a computer system, for example, the computer system that perform the functions described herein can be generically considered as one or more controllers that control such functions. The one or more controllers can be implemented in numerous ways, such as with dedicated hardware and/or firmware, using a processor that is programmed using microcode or software to perform the functions recited above or any suitable combination of the foregoing.

Each of the systems described herein, and components thereof, may be implemented using any of a variety of technologies, including software (e.g., C, C#, C++, Java, or a combination thereof), hardware (e.g., one or more application-specific integrated circuits), firmware (e.g., electrically-programmed memory) or any combination thereof. One or more of the components may reside on a single device (e.g., a computer), or one or more components may reside on separate, discrete devices. Further, each component may be distributed across multiple devices, and one or more of the devices may be interconnected.

Further, on each of the one or more devices that include one or more components of the systems, each of the components may reside in one or more locations on the system. For example, different portions of the components of these systems may reside in different areas of memory (e.g., RAM, ROM, disk, etc.) on the device. Each of such one or more devices may include, among other components, a plurality of known components such as one or more processors, a memory system, a disk storage system, one or more network interfaces, and one or more busses or other internal communication links interconnecting the various components.

The systems, and components thereof, may be implemented using a computer system such as that described below.

Various embodiments according to the invention may be implemented on one or more computer systems. These computer systems, may be, for example, general-purpose computers such as those based on Intel PENTIUM-type and XScale-type processors, Motorola PowerPC, Motorola DragonBall, IBM HPC, Sun UltraSPARC, Hewlett-Packard PA-RISC processors, any of a variety of processors available from Advanced Micro Devices (AMD) or any other type of processor. They may include single core or multi-core processors. It should be appreciated that one or more of any type of computer system may be used to implement various embodiments of the invention.

A general-purpose computer system according to one embodiment of the invention is configured to perform any of the functions described above. It should be appreciated that the system may perform other functions and the invention is not limited to having any particular function or set of functions.

Figure 10:
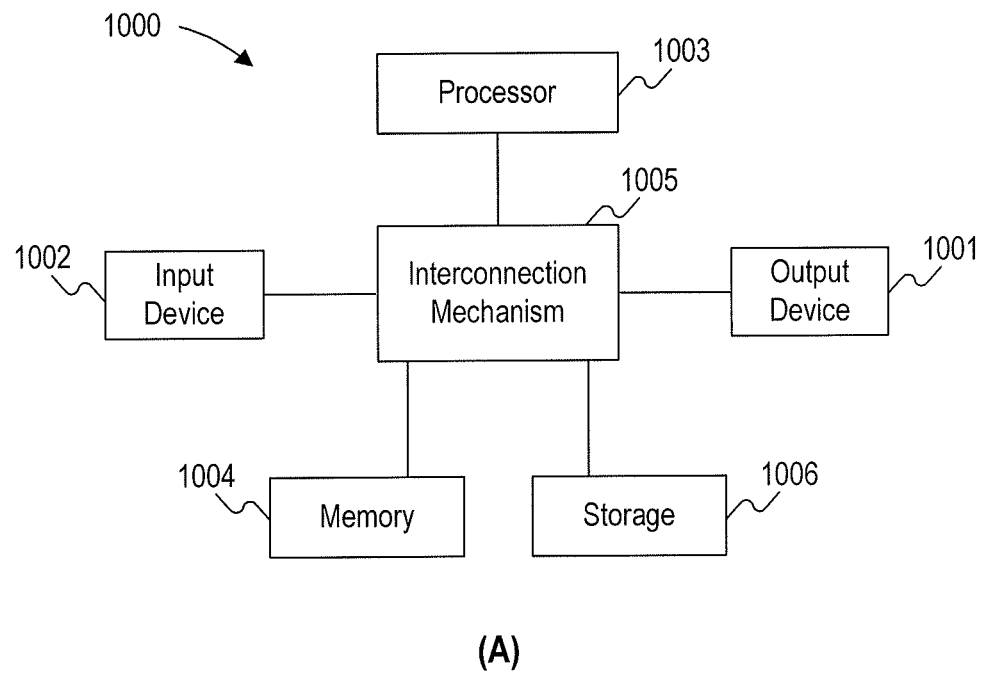
FIG. 10 (parts A and B) is a block diagram of a typical computer system that might be used to practice aspects of the invention that are computer-implemented, though the invention is not limited to any particular computer system.
Figure 10:
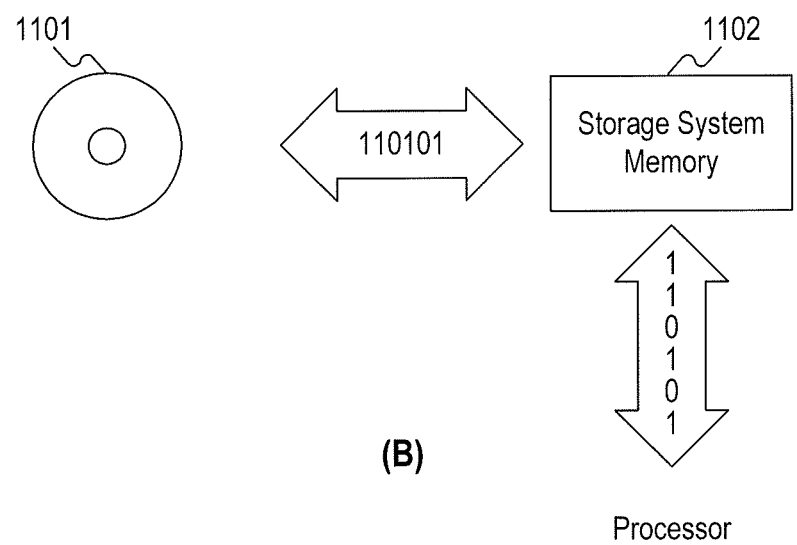

For example, various aspects of the invention may be implemented as specialized software executing in a general-purpose computer system 1000 such as that shown in FIG. 10. The computer system 1000 may include a processor 1003 connected to one or more memory devices 1004, such as a disk drive, memory, or other device for storing data. Memory 1004 is typically used for storing programs and data during operation of the computer system 1000. Components of computer system 1000 may be coupled by an interconnection mechanism 1005, which may include one or more busses (e.g., between components that are integrated within a same machine) and/or a network (e.g., between components that reside on separate discrete machines). The interconnection mechanism 1005 enables communications (e.g., data, instructions) to be exchanged between system components of system 1000. Computer system 1000 also includes one or more input devices 1002, for example, a keyboard, mouse, trackball, microphone, touch screen, and one or more output devices 1001, for example, a printing device, display screen, speaker. In addition, computer system 1000 may contain one or more interfaces (not shown) that connect computer system 1000 to a communication network (in addition or as an alternative to the interconnection mechanism 1005.

The storage system 1006 typically includes a computer readable and writeable nonvolatile recording medium 1101 in which signals are stored that define a program to be executed by the processor or information stored on or in the medium 1101 to be processed by the program. The medium may, for example, be a disk or flash memory. Typically, in operation, the processor causes data to be read from the nonvolatile recording medium 1101 into another memory 1102 that allows for faster access to the information by the processor than does the medium 1101. This memory 1102 is typically a volatile, random access memory such as a dynamic random access memory (DRAM) or static memory (SRAM). It may be located in storage system 1006, as shown, or in memory system 1004, not shown. The processor 1003 generally manipulates the data within the integrated circuit memory 1004, 1102 and then copies the data to the medium 1101 after processing is completed. A variety of mechanisms are known for managing data movement between the medium 1101 and the integrated circuit memory element 1004, 1102, and the invention is not limited thereto. The invention is not limited to a particular memory system 1004 or storage system 1006.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although computer system 1000 is shown by way of example as one type of computer system upon which various aspects of the invention may be practiced, it should be appreciated that aspects of the invention are not limited to being implemented on the computer system as shown. Various aspects of the invention may be practiced on one or more computers having a different architecture or components than that shown.

Computer system 1000 may be a general-purpose computer system that is programmable using a high-level computer programming language. Computer system 1000 may be also implemented using specially programmed, special purpose hardware. In computer system 1000, processor 1003 is typically a commercially available processor such as a well-known Pentium class processor available from the Intel Corporation. Many other processors are available. Such a processor usually executes an operating system which may be, for example, the Windows® 95, Windows® 98, Windows NT®, Windows® 2000 (Windows® ME), Windows® XP, Windows CE® or Pocket PC® operating systems available from the Microsoft Corporation; MAC OS® System X available from Apple Computer; the Solaris® Operating System available from Sun Microsystems; Linux available from various sources; UNIX available from various sources; or Palm OS available from Palmsource. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL) or interpreted (e.g., Java) code which communicate over a communication network (e.g., the Internet) using a communication protocol (e.g., TCP/IP).

It should be appreciated that the invention is not limited to executing on any particular system or group of systems. Also, it should be appreciated that the invention is not limited to any particular distributed architecture, network, or communication protocol.

Various embodiments of the present invention may be programmed using an object-oriented programming language, such as SmallTalk, Java, C++, Ada, or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented as programmed or non-programmed elements, or any combination thereof. Further, various embodiments of the invention may be implemented using Microsoft.NET technology available from Microsoft Corporation.

Among the advantages of the approach, system and method discussed above are the following: a unique design solution (for implant, abutment and crown or implant and abutment-crown, or individual components) is optimized with little or no operator input; the effects of all parameter changes are quantified with the same metric; the effects of dental context and clinician preference can be introduced as adjustable weights that are applied to specific parameters; hard constraints can be implemented by using high values for the metric or additional functional parameters when the parameters exceed predefined limits; and standard single-parameter optimization search algorithms may be employed. A superior match between abutment and crown and adherence to the clinician's design rules should result in better and more consistent aesthetics than previous computer-aided designs have achieved. One should obtain components and an overall combination of them that is at least equal to what a skilled technician can provide, at lower cost than a handmade product.

Having thus described the invention and various illustrative embodiments and uses as well as some of its advantages and optional features, it will be apparent that such embodiments are presented by way of example only and not by way of limitation. Those persons skilled in the art will readily devise alterations and improvements on these embodiments, such as variations on the disclosed methods and systems, as well as additional embodiments, without departing from the spirit and scope of the invention. It is impossible to enumerate all of the variations that will quite quickly occur to those in the art. Accordingly, the invention is limited only as defined in the following claims and equivalents thereto.

What is claimed is:

1. A computer-implemented method for specifying design parameters for at least first and second dental restoration components, the at least first and second dental restoration components being installed in a cooperating relationship, and the first dental restoration component being configured to support the second dental restoration component in the cooperating relationship, said method comprising:
 a. receiving, by a processor, a set of design dimensional constraints which must be satisfied for each of the first and second dental restoration components;
 b. receiving, by the processor, a set of design parameters to be assigned for each of the first and second dental restoration components;
 c. for the first dental restoration component, assigning, by the processor, a value to each of the design parameters, consistent with the constraints for the first dental restoration component;
 d. for the second dental restoration component, determining, by the processor, whether there is a conflict between possible values for a design parameter and the design dimensional constraints for the first dental restoration component and if there is a conflict, changing a value of at least one design parameter for the first dental restoration component and re-determining whether there is a conflict, until no conflicts exist;
 e. assigning, by the processor, a value to a first design parameter of the second dental restoration component, consistent with all constraints; and
 f. executing a penalty function to calculate an acceptable set of design parameter values until values have been assigned to all design parameters of the first dental restoration component and the second dental restoration component and no constraint or parameter value conflicts exist;
wherein the penalty function includes at least one property selected from the group consisting of having the set of design parameter values that are continuous and increase monotonically away from a center value; at a center value, the parameter value is minimum and near zero, as is its first derivative; the parameter value has a continuously and monotonically increasing first derivative or decreasing for negative deviations, within a range of interest; at specified parameter values of the first design parameter or second design parameter, both above and below a center value, the penalty function has a value of unity and a controlled first derivative; at predetermined limit values for the first design parameter or second design parameter, both above and below a center value, the penalty function has specified penalty values and specified first derivatives; and has specified slopes beyond the limit values, equal to a first derivatives at the limit values; and
wherein the first and second dental restoration components are an abutment and a crown, respectively, and wherein the abutment is configured to connect the crown to a dental implant.

2. The method of claim 1, further including recording said assigned parameter values in a data structure on a computer-readable medium.

3. The method of claim 2, further including operating a computer-aided manufacturing system in accordance with said values in said data structure, to manufacture said first and second components.

4. The method of claim 1, wherein the at least one common design feature is a common margin for the abutment and crown.

5. The method of claim 1, further including recording said assigned parameter values in a data structure on a computer-readable medium.

6. The method of claim 5, further including operating a computer-aided manufacturing system in accordance with said values in said data structure, to manufacture at least one of said first and second components.

7. A non-transitory computer-readable storage medium having stored thereon instructions, which, when executed, cause a computer system to perform a method of specifying design parameters for at least first and second dental restoration components, the at least first and second dental restoration components being installed in a cooperating relationship, and the first dental restoration component being configured to support the second dental restoration component in the cooperating relationship, comprising:
 a. receiving a set of design dimensional constraints which must be satisfied for each of the first and second dental restoration components;

b. receiving a set of design parameters to be assigned for each of the first and second dental restoration components;

c. for the first dental restoration component, assigning a value to each of said design parameters, consistent with the constraints for said component;

d. for the second dental restoration component, determining whether there is a conflict between possible values for a design parameter and the dimensional constraints for the first component and, if there is a conflict, changing a value of at least one design parameter for the first component and re-determining whether there is a conflict, until no conflict exists or it is established that for all values of the design parameters for the first component there will be conflict;

e. assigning a value to a first design parameter of the second dental restoration component, consistent with all constraints; and f. executing a penalty function to calculate an acceptable set of design parameter values until values have been assigned to all design parameters of the first dental restoration component and the second dental restoration component and no constraint or parameter value conflicts exist;

wherein the penalty function is asymmetric such that the penalty function forces the design parameter to the desired value unless other design parameters are forcing it away from the desired value;

wherein the penalty function includes at least one property selected from the group consisting of having the set of design parameter values that are continuous and increase monotonically away from a center value: at a center value, the parameter value is minimum and near zero, as is its first derivative: the parameter value has a continuously and monotonically increasing first derivative or decreasing for negative deviations, within a range of interest: at specified parameter values of the first design parameter or second design parameter, both above and below a center value, the penalty function has a value of unity and a controlled first derivative; at predetermined limit values for the first design parameter or second design parameter, both above and below a center value, the penalty function has specified penalty values and specified first derivatives; and has specified slopes beyond the limit values, equal to a first derivatives at the limit values; and wherein the first and second dental restoration components are an abutment and a crown, respectively, and wherein the abutment is configured to connect the crown to a dental implant.

8. The article of claim 7, wherein said method further includes operating a computer-aided manufacturing system in accordance with said assigned values, to manufacture at least one of said first and second components.

9. The article of claim 7, wherein the first and second dental restoration components comprise an abutment and a crown, wherein the abutment is configured to connect the crown to a dental implant and wherein the at least one common design feature is a common margin for the abutment and crown.

10. A dental restoration abutment and a corresponding, paired dental restoration crown which when assembled together share between them a common margin, made using the process of any of claims 4.

11. The method of claim 1, further including operating a computer-aided manufacturing system in accordance with said assigned values in said data structure, to manufacture at least one of said first and second dental restoration components.

12. The article of claim 7, wherein said method further includes operating a computer-aided manufacturing system in accordance with said assigned values, to manufacture at least one of said first and second dental restoration components.

13. A dental restoration component made using the process of any of claims 1, 4, and 11.

* * * * *